United States Patent
Rowe et al.

(10) Patent No.: US 9,546,192 B2
(45) Date of Patent: Jan. 17, 2017

(54) LIGATED ANIONIC-ELEMENT REAGENT COMPLEXES (LAERCS) AS NOVEL REAGENTS

(71) Applicants: Toyota Motor Engineering & Manufacturing North America, Inc., Erlanger, KY (US); The University of Manitoba, Winnipeg (CA)

(72) Inventors: Michael Paul Rowe, Pinckney, MI (US); Elizabeth Marie Skoropata, Winnipeg (CA); Yaroslav Stephan Wrocyznskyj, Winnipeg (CA); Johan Alexander van Lierop, Winnipeg (CA)

(73) Assignees: Toyota Motor Engineering & Manufacturing North America, Inc., Erlanger, KY (US); The University of Manitoba, Winnipeg (CA)

(*) Notice: Subject to any disclaimer, the term of this patent is extended or adjusted under 35 U.S.C. 154(b) by 57 days.

(21) Appl. No.: 14/593,371

(22) Filed: Jan. 9, 2015

(65) Prior Publication Data

US 2016/0200753 A1 Jul. 14, 2016

(51) Int. Cl.
| | |
|---|---|
| C07F 19/00 | (2006.01) |
| B22F 1/00 | (2006.01) |
| B22F 9/04 | (2006.01) |
| B22F 9/20 | (2006.01) |

(52) U.S. Cl.
CPC ............ *C07F 19/005* (2013.01); *B22F 1/0003* (2013.01); *B22F 9/04* (2013.01); *B22F 9/20* (2013.01); *B22F 2009/043* (2013.01)

(58) Field of Classification Search
CPC .... C07C 255/03; C07F 19/005; B22F 1/0003; B22F 9/04; B22F 9/20

USPC .............................. 556/8; 423/276, 284, 286
See application file for complete search history.

(56) References Cited

U.S. PATENT DOCUMENTS

| | | |
|---|---|---|
| 7,041,350 B1 | 5/2006 | Rule et al. |
| 7,785,392 B2 | 8/2010 | Shim et al. |
| 8,192,866 B2 | 6/2012 | Golightly et al. |
| 8,372,177 B1 | 2/2013 | Thoma et al. |
| 8,395,003 B2 | 3/2013 | Leger et al. |
| 9,142,834 B2 | 9/2015 | Mohtadi et al. |

(Continued)

FOREIGN PATENT DOCUMENTS

| | | |
|---|---|---|
| CN | 102909381 A | 6/2013 |
| JP | 2013-073839 A | 4/2013 |

(Continued)

OTHER PUBLICATIONS

Rowe et al., "Stable Complexes of Zero-Valent Metal and Hydride as Novel Reagents" U.S. Appl. No. 14/046,0861, filed Oct. 4, 2014.

(Continued)

*Primary Examiner* — Porfirio Nazario Gonzalez
(74) *Attorney, Agent, or Firm* — Christopher G. Darrow; Darrow Mustafa PC

(57) ABSTRACT

A novel ligated reagent complex is provided. The ligated reagent includes at least one zero-valent atom, whether metal, metalloid, or non-metal, in complex with at least one hydride molecule and at least one nitrile compound. The ligated reagent complex can be useful in the synthesis of nanoparticles. Also provided is a method for preparing a ligated reagent complex. The method includes a step of ball-milling a mixture that includes a preparation containing a zero-valent element, a hydride molecule, and a nitrile compound.

20 Claims, 2 Drawing Sheets

(56) References Cited

U.S. PATENT DOCUMENTS

| | | |
|---|---|---|
| 2005/0217427 A1 | 10/2005 | Suthersan et al. |
| 2009/0029148 A1 | 1/2009 | Hashimoto et al. |
| 2009/0090214 A1 | 4/2009 | Cheng |
| 2009/0264277 A1 | 10/2009 | Raj et al. |
| 2013/0084502 A1 | 4/2013 | Singh et al. |
| 2015/0068646 A1 | 3/2015 | Rowe |
| 2015/0098884 A1 | 4/2015 | Rowe |
| 2015/0098885 A1 | 4/2015 | Rowe |
| 2015/0099135 A1 | 4/2015 | Mohtadi et al. |
| 2015/0099172 A1 | 4/2015 | Rowe et al. |
| 2015/0099183 A1 | 4/2015 | Singh et al. |

FOREIGN PATENT DOCUMENTS

| | | |
|---|---|---|
| WO | WO2011150212 A2 | 12/2011 |
| WO | 2012007830 A1 | 1/2012 |
| WO | WO2013056185 A1 | 4/2013 |
| WO | WO2013063161 A2 | 5/2013 |

OTHER PUBLICATIONS

Rowe et al., "Stable Complexes of Zero-Balent Metallic Element and Hydride as Novel Reagents" U.S. Appl. No. 14/219,823, filed Mar. 19, 2014.

Rowe et al. "Stable Complexes of Non-Metal Elements and Hydride as Novel Reagents" U.S. Appl. No. 14/269,909, filed May 5, 2014.

Schuth et al., "Light metal hydrides and complex hydrides for hydrogen storage", Sep. 21, 2004, pp. 2249-2258.

Imamura et al., "Dehydriding of Sn/MgH2 nanocomposite formed by ball milling of mgH2 with Sn", Int. J. Hydrogen Energy, 32, 4191-4194.

Wronski et al., "A new nanonickel catalyst for hydrogen storage in solid-state magnesium hydrides", Int. J. Hydrogen Energy, 36, 1159-1166.

Chen et al., "Improved Dehydrogenation Properties of Ca(BH4)2•nNH3 (n=1, 2, and 4) Combined with Mg(BH4)2", J. Phys. Chem., 116, 21162-21168.

Varin et al., "The effects of ball milling and nanometrick nickel additive on the hydrogen desorption from lithium borohydride and manganese chloride (3LiBH4+MnCl2) mixture", Int. J. Hydrogen Energy, 35 (2010) 3588-3597.

Rowe et al., "Synthesis of Ferromagnetic Manganese—Bismuth Nanoparticles Using a Manganese-Based Ligated Anionic-Element Reagent Complex (Mn-LAERC) and Formation of Mulk MnBi Magnets Therefrom", U.S. Appl. No. 14/593,583, filed Jan. 9, 2015.

Poudyal et al.; "Advances in Nanostructured Permanent Magnets Research"; Journal of Physics D: Applied Physics; Dec. 14, 2012; in 23 pages; vol. 46; No. 4.

Suzuki et al. "Spin Reorientation Transition and Hard Magnetic Properties of MnBi Intermetallic Compound", J. Appl. Phys., 111 Article No. 07E303, Feb. 8, 2012, 3 pages.

Yang et al. "Temperature Dependences of Structure and Coercivity for Melt-spun MnBi Compound" J. Magnetism Magnet. Mat., 330, pp. 106-110, Nov. 5, 2012.

Yang et al. "Anisotropic Nanocrystalline MnBi With High Coercivity at High Temperature", Appl. Phys. Lett., 99, Article No. 082505, Aug. 25, 2011, 4 pages.

LIGATED ANIONIC-ELEMENT REAGENT COMPLEXES (LAERCS) AS NOVEL REAGENTS

TECHNICAL FIELD

The present disclosure relates in general to a reagent complex composed of a zero-valent element in stable complex with one or more hydride molecules and one or more nitrile compounds and to a method of forming the complex.

BACKGROUND

Previous disclosures have described a novel reagent complex having the general formula $Q^0 \cdot X_y$, where $Q^0$ is a zero-valent element (i.e. an elemental solid) and X is a hydride molecule such as $LiBH_4$. This type of reagent complex, which can be termed an AERC (Anionic Element Reducing Complex) has been shown to be useful in the facile and reproducible synthesis of nanoparticles containing the zero-valent element $Q^0$. Modifications to the AERC which improve its reactivity would be desirable.

SUMMARY

Ligated reagent complexes and nanoparticles synthesized using the ligated reagent complexes are disclosed.

In one aspect, a composition is disclosed. The composition comprises a complex according to Formula I:

$$Q^0 \cdot X_y \cdot L_z \qquad \text{I,}$$

wherein $Q^0$ is a zero-valent element, X is a hydride, L is a nitrile, y is an integral or fractional value greater than zero, and z is an integral or fractional value greater than zero. In some variations, the zero-valent element is a non-metal or a metalloid. In some instances, the hydride can be lithium borohydride, and each of y and z can be equal to or less than about 4.

In another aspect, a method for preparing a ligated reagent complex is disclosed. The method includes a step of ball-milling a mixture that contains a preparation containing a zero-valent element, a hydride molecule, and a nitrile compound. An organic solvent can optionally be included in the mixture.

In yet another aspect, a composition that is prepared by a method is disclosed. The composition comprises a complex according to Formula I:

$$Q^0 \cdot X_y \cdot L_z \qquad \text{I,}$$

wherein $Q^0$ is a zero-valent element, X is a hydride, L is a nitrile, y is an integral or fractional value greater than zero, and z is an integral or fractional value greater than zero. The method of preparing the composition includes a step of ball-milling a mixture that contains a preparation containing a zero-valent element, a hydride molecule, and a nitrile compound.

BRIEF DESCRIPTION OF THE DRAWINGS

Various aspects and advantages of the invention will become apparent and more readily appreciated from the following description of the embodiments taken in conjunction with the accompanying drawings, of which.

DETAILED DESCRIPTION

Figure 1:
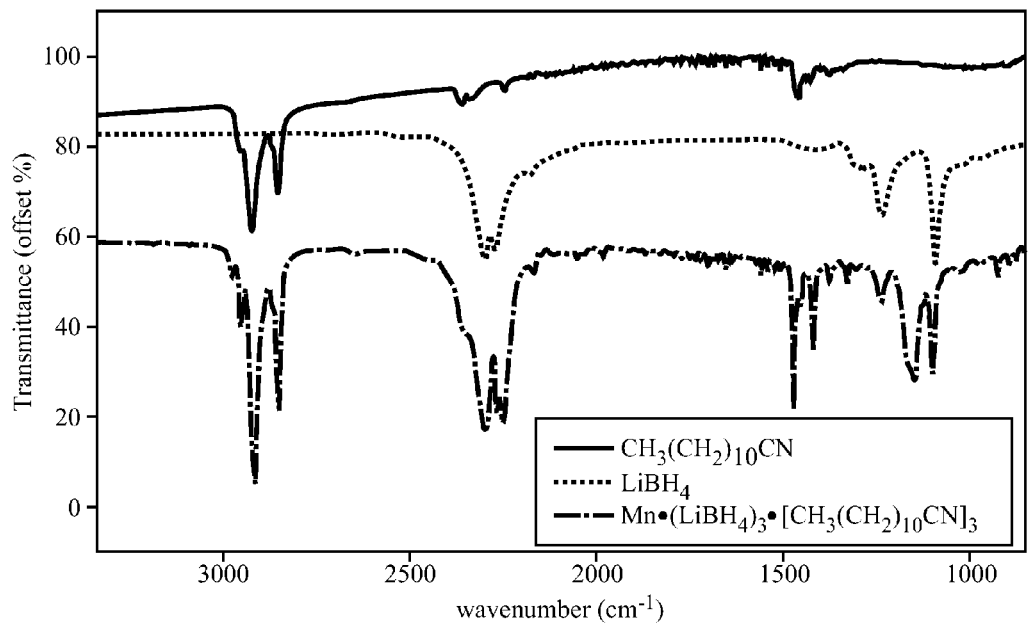
FIG. 1 is a series of three infrared (IR) spectra of a representative nitrile, of a representative hydride, and of a ligated reagent complex according to the present disclosure having the nitrile and the hydride.

The present disclosure describes ligated reagent complexes useful in the synthesis of elemental nanoparticles and methods of forming the ligated reagent complexes. The ligated reagent complexes include a zero-valent element, a hydride molecule, and a nitrile. The methods of forming the ligated reagent complexes include a step of ball-milling a mixture that includes each of the aforementioned components. Inclusion of the nitrile can improve the reactivity of the resulting ligated reagent complex for the subsequent formation of nanoparticles in comparison to a non-ligated reagent complex.

As the term will be used herein, "zero-valent" or "zero-valent element" refers to the condition of being in oxidation state zero. More generically, the phrase "zero-valent" as used herein refers to the condition of the material so described of being in elemental form.

As used herein, the term "element" refers to any element of the periodic table. In particular, it refers to any element which, in its zero-valent form, is a solid or liquid under the conditions of use. More particularly still, the term "element", as used herein, refers to any element which is solid or liquid under standard conditions of temperature and pressure, for example 25° C. and 1 atm.

The phrase "metallic element" refers to a metal, a lanthanide, or a metalloid. A "metal" can refer to an alkaline earth metal, an alkali metal, a transition metal, or a post-transition metal. The phrase "transition metal" can refer to any D-block metal of Groups 3 through 12. The phrase "post-transition metal" can refer to Group 13 through 16 metals. The term "metalloid" can refer to any of boron, silicon, germanium, arsenic, antimony, tellurium, or polonium.

As used herein, the term "hydride", or "hydride molecule", refers generally to any molecular species capable of functioning as a hydrogen anion donor. In different instances, a hydride as referenced herein can be a binary metal hydride or "salt hydride" (e.g. NaH, or $MgH_2$), a binary metalloid hydride (e.g. $BH_3$), a complex metal hydride (e.g. $LiAlH_4$), or a complex metalloid hydride (e.g. $LiBH_4$ or $Li(CH_3CH_2)_3BH$). In some examples the hydride will be $LiBH_4$. The term hydride as described above can in some variations include a corresponding deuteride or tritide.

The term "nitrile", as used herein, refers to a molecule having the formula R—CN. In different implementations, R can be a substituted or unsubstituted alkyl or aryl group, including but not limited to: a straight-chain, branched, or cyclic alkyl or alkoxy; or a monocyclic or multicyclic aryl or heteroaryl. In some implementations, the R group of a nitrile will be a straight chain alkyl. In one particular implementation, the nitrile will be $CH_3(CH_2)_{10}CN$, alternatively referred to as dodecane nitrile or undecyl cyanide.

A composition is disclosed, comprising a complex according to Formula I:

$$Q^0 \cdot X_y \cdot L_z \qquad \text{I,}$$

wherein $Q^0$ is a zero-valent element, wherein X is a hydride, and wherein y is an integral or fractional value greater than zero. The complex according to Formula I is alternatively referred to below as a "ligated reagent complex" or a LAERC (Ligated Anionic Element Reagent Complex).

The value y according to Formula I defines the stoichiometry of hydride molecules to zero-valent elemental atoms in the complex. The value of y can include any integral or fractional value greater than zero. In some instances, y can be less than or equal to 4. In some particular instances, y can equal 3.

The value z according to Formula I defines the stoichiometry of nitrile molecules to zero-valent elemental atoms in the complex. The value of z can include any integral or fractional value greater than zero. In some instances, z can be less than or equal to 4 and in some particular instances, z can equal 3. In some instances, y can equal z.

As noted, the ligated reagent complexes can have improved reactivity in comparison to previously disclosed non-ligated reagent complexes having the formula $Q^0.X_y$, where Q, X, and y are as described above. Without being bound to any particular theory, it is believed that inclusion of the nitrile may provide a smaller, more uniform, or otherwise more favorable particle size or form of the reagent.

The ligated reagent complexes of the present disclosure can have any supramolecular structure, or no supramolecular structure. For example, the ligated reagent complex can exist as a supramolecular cluster of many zero-valent elemental atoms interspersed with hydride molecules and/or nitrile compounds. The ligated reagent complex could exist as a cluster of zero-valent elemental atoms in which the cluster is surface-coated with hydride molecules and/or nitrile compounds. The ligated reagent complex could exist as individual zero-valent elemental atoms having little to no molecular association with one another, but each being associated with hydride molecules and nitrile compounds according to Formula I. Any of these microscopic structures, or any other structure consistent with Formula I, is intended to be within the scope of the present disclosure.

Additionally disclosed is a method for synthesizing a ligated reagent complex of the type described above. The method includes a step of ball-milling a mixture that includes a preparation containing a zero-valent element, a hydride molecule, and a nitrile. Performance of the method will generally produce a ligated reagent complex of the type disclosed above and having a formula as defined above by Formula I.

In some instances, the ball-milling step can be performed in an oxygen-free environment, in an anhydrous environment, or in an environment that is oxygen-free and anhydrous, such as under argon or under vacuum. An oxygen-free and/or anhydrous environment can potentially limit undesired oxidation of the resulting ligated reagent complex.

In some instances, the mixture to be ball-milled can include a 1:1:1 molar ratio of zero-valent elemental atoms, hydride molecules, and nitrile compounds. In some instances, the mixture can include hydride molecules, nitrile compounds, or both in molar excess relative to atoms of the zero-valent element. In some such instances, such molar excess can be about 4-fold or less. In some instances, the mixture to be ball-milled can include a 1:3:3 molar ratio of zero-valent elemental atoms, hydride molecules, and nitrile compounds.

The preparation containing a zero-valent element can be any composition consisting substantially of a zero-valent metal. In many instances the preparation containing a zero-valent element will include zero-valent metal in a form which possesses a high surface-area-to-mass ratio. In some instances the zero-valent element will be present in a powder form. It is contemplated that the preparation containing a zero-valent element can be a highly porous elemental solid, an elemental solid with a honeycomb structure, or some other preparation with a high surface-area-to-mass ratio.

In some instances the preparation containing a zero-valent element will be a preparation containing a zero-valent transition metal, such as an elemental transition metal in powder form. Suitable transition metals include, but are not limited to cadmium, cobalt, copper, chromium, iron, manganese, gold, silver, platinum, titanium, nickel, niobium, molybdenum, rhodium, palladium, scandium, vanadium, and zinc. In some instances the preparation containing a zero-valent metal can include a zero-valent post-transition metal. Suitable post-transition metals include aluminum, gallium, indium, tin, thallium, lead, or bismuth. In some implementations, the preparation containing a zero-valent element can be a preparation containing zero-valent manganese.

Without being bound by any particular theory, it is believed that the nitrile, L, of the disclosed ligated reagent complex can function to ablate or otherwise assist in decreasing the particle size of the zero-valent element and/or the reagent complex.

In an Example, elemental manganese powder can be combined with lithium borohydride and with dodecane nitrile in a 1:3:3 molar ratio. A solvent can be added, and the combination can then be ball-milled in an inert environment for four hours. The resulting product is the complex $Mn^0Li(BH_4)_3.[CH_3(CH_2)_{10}CN]_3$. FIG. 1 shows infrared (IR) spectra of the dodecane nitrile, lithium borohydride, and $Mn.Li(BH_4)_3.[CH_3(CH_2)_{10}CN]_3$ ligated reagent complex. As shown in FIG. 1, the ligated reagent complex has several shifted and/or new peaks relative to the nitrile and hydride spectra, indicating formation of the ligated reagent complex. For example, new peaks centered at about 1147, 1163, and 2978 $cm^{-1}$ in the ligated reagent complex spectrum are not present in the nitrile or hydride spectra.

Figure 2A:
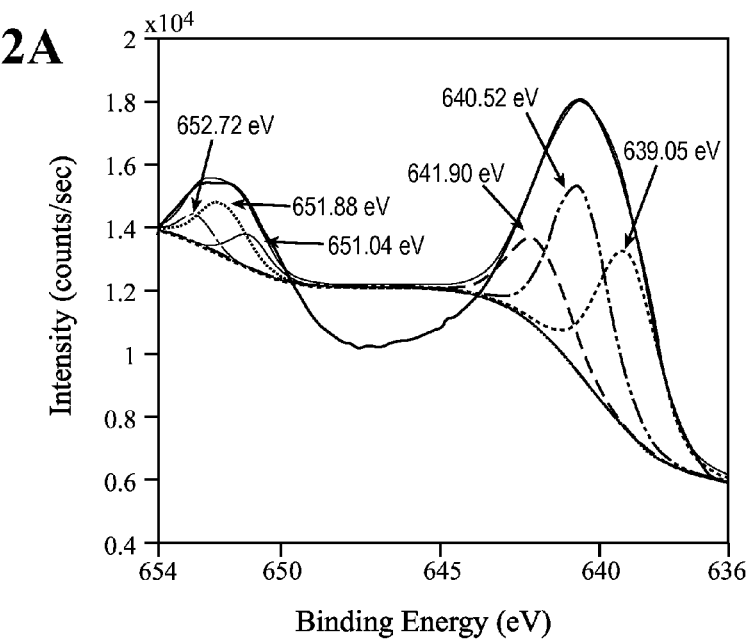
FIG. 2A is an x-ray photoelectron spectrum of manganese powder.
Figure 2B:
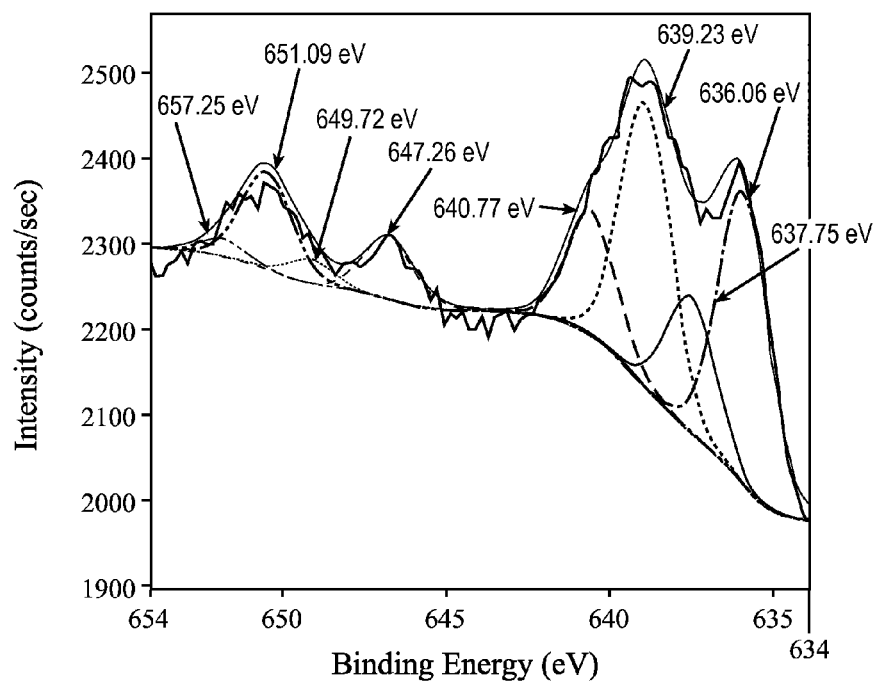
FIG. 2B is an x-ray photoelectron spectrum of a non-ligated reagent complex, $Mn \cdot (LiBH_4)_2$.
Figure 2C:
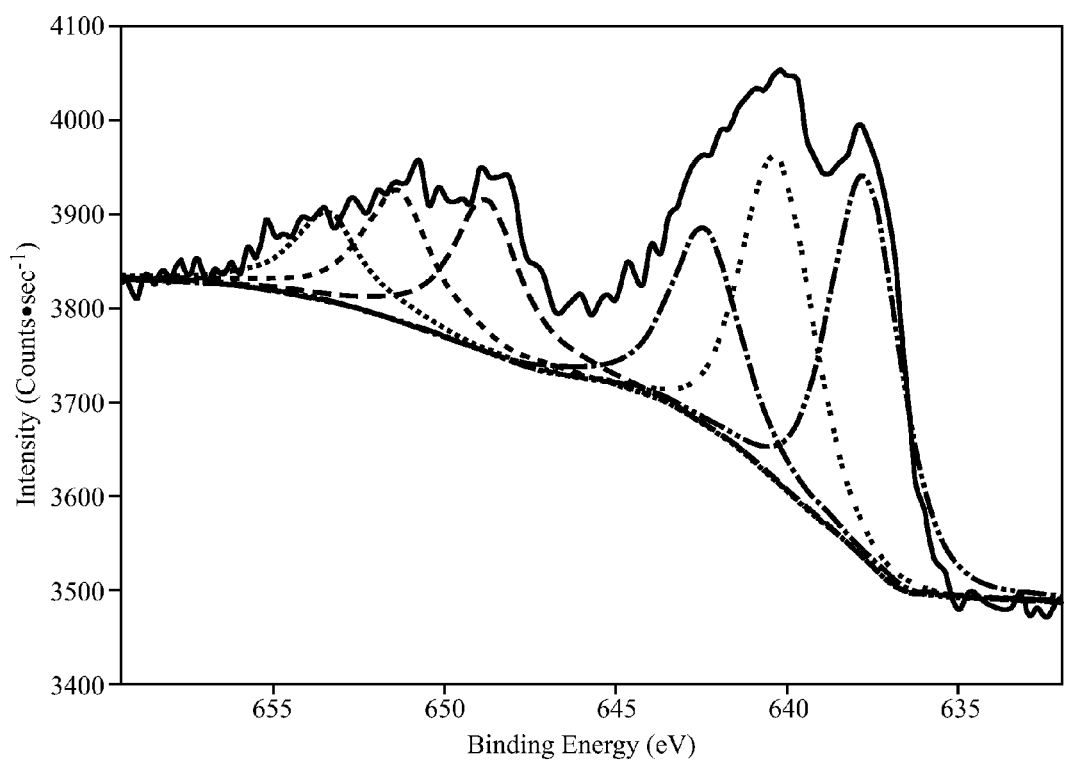
FIG. 2C is an x-ray photoelectron spectrum of the ligated reagent complex of FIG. 1, $Mn \cdot (LiBH_4)_3 \cdot [CH_3(CH_2)_{10}CN]_3$.

FIGS. 2A-C show manganese-region x-ray photoelectron spectra of elemental manganese, a $Mn^0.Li(BH_4)_2$ (non-ligated) reagent complex lacking nitrile, and the $Mn^0.Li(BH_4)_3.[CH_3(CH_2)_{10}CN]_3$ ligated reagent complex of the present disclosure, respectively. In each case, the highest solid line represents the acquired spectrum and the various dashed or dotted lines represent deconvoluted peaks. The $Mn^0.Li(BH_4)_2$ reagent complex of FIG. 2B, disclosed previously, was prepared by ball-milling a mixture of manganese powder and lithium borohydride without a nitrile present. Comparison of the spectrum of FIG. 2C to the spectra of FIGS. 2A and 2B again supports formation of the ligated reagent complex. For example, in comparison to the manganese powder spectrum of FIG. 2A, the ligated reagent complex spectrum of FIG. 2C has a new peak centered at about 637.95 eV.

Also disclosed is a ligated reagent complex according to Formula I which is prepared by the disclosed method for synthesizing a ligated reagent complex. The ligated reagent complex and the method for synthesizing a ligated reagent complex are as described above.

It is to be noted that the ligated reagent complex of the present disclosure is a suitable reagent for the synthesis of nanoparticles containing the zero-valent element, $Q^0$. For example, if $Q^0$ is a zero-valent metal, $M^0$, and a second, cationic metal, $M'^+$, is added to the ligated reagent complex, the mixture can spontaneously form metal nanoparticles of alloyed composed of an alloy $M^0$ and $M'$, the metal $M'$ having been reduced to zero-valent form.

The present invention is further illustrated with respect to the following examples. It needs to be understood that these examples are provided to illustrate specific embodiments of the present invention and should not be construed as limiting the scope of the present invention.

Example 1

$Mn^0 \cdot Li(BH_4)_3 \cdot [CH_3(CH_2)_{10}CN]_3$ Synthesis 0.496 g of manganese powder, 0.592 g of lithium borohydride, 4.912 g of dodecane nitrile and 6 mL of toluene are added to a ball mill jar under argon. The mixture is milled at 300 rpm for 4 hours. An IR spectrum of the resulting complex is shown in FIG. 1 and an XPS spectrum of the resulting complex is shown in FIG. 2C.

The foregoing description relates to what are presently considered to be the most practical embodiments. It is to be understood, however, that the disclosure is not to be limited to these embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A composition comprising a complex according to a formula, $$Q^0 \cdot X_y \cdot L_z,$$

wherein $Q^0$ is a zero-valent element, X is a hydride, y is an integral or fractional value greater than zero, L is a nitrile, and z is an integral or fractional value greater than zero; and wherein the hydride can be any of a binary metal hydride, a binary metalloid hydride, a complex metal hydride, and a complex metalloid hydride.

2. The composition as recited in claim 1, wherein $Q^0$ is a transition metal.

3. The composition as recited in claim 1, wherein $Q^0$ is manganese.

4. The composition as recited in claim 1, wherein X is lithium borohydride.

5. The composition as recited in claim 1, wherein L is dodecane nitrile.

6. The composition as recited in claim 1, wherein each of y and z is about 4 or less.

7. A method for synthesizing a reagent complex, comprising:
    ball-milling a mixture containing a preparation containing a zero-valent metal, a hydride and a nitrile.

8. The method as recited in claim 7, wherein the hydride is a complex metal hydride or a complex metalloid hydride.

9. The method as recited in claim 7, wherein the hydride is lithium borohydride.

10. The method as recited in claim 7, wherein the hydride and the preparation containing a zero-valent metal are mixed in substantially equimolar proportion.

11. The method as recited in claim 7, wherein the hydride is mixed with the preparation containing a zero-valent metal in about four-fold or lower molar excess.

12. The method as recited in claim 7, wherein the ball-milling is performed in an oxygen-free environment, in an anhydrous environment, or in an environment that is oxygen-free and anhydrous.

13. The method as recited in claim 7, wherein the preparation containing a zero-valent metal is a preparation containing a transition metal.

14. The method as recited in claim 7, wherein the preparation containing a zero-valent metal is a preparation containing manganese.

15. A ligated reagent complex prepared by a method comprising:
    ball-milling a mixture of a hydride with a preparation containing a zero-valent metal.

16. The ligated reagent complex as recited in claim 15, wherein the hydride is a complex metal hydride or a complex metalloid hydride.

17. The ligated reagent complex as recited in claim 15, wherein the hydride is lithium borohydride.

18. The ligated reagent complex as recited in claim 15, wherein the ball-milling is performed in an oxygen-free environment, in an anhydrous environment, or in an environment that is oxygen-free and anhydrous.

19. The ligated reagent complex as recited in claim 15, wherein the preparation containing a zero-valent metal is a preparation containing a transition-metal.

20. The ligated reagent complex as recited in claim 15, wherein the preparation containing a zero-valent metal is a preparation containing manganese.

* * * * *